(12) United States Patent
Gross

(10) Patent No.: US 7,244,241 B2
(45) Date of Patent: Jul. 17, 2007

(54) METHOD AND MEANS FOR CEMENTING A LINER ONTO THE FACE OF THE GLENOID CAVITY OF A SCAPULA

(76) Inventor: R. Michael Gross, 1726 S. 87th St., Omaha, NE (US) 68124

( * ) Notice: Subject to any disclaimer, the term of this patent is extended or adjusted under 35 U.S.C. 154(b) by 0 days.

(21) Appl. No.: 10/046,592

(22) Filed: Jan. 14, 2002

(65) Prior Publication Data

US 2002/0058946 A1 May 16, 2002

Related U.S. Application Data

(62) Division of application No. 09/563,613, filed on May 2, 2000, now Pat. No. 6,506,214.

(51) Int. Cl.
*A61M 1/00* (2006.01)
(52) U.S. Cl. ............................ 604/35; 604/313; 606/93
(58) Field of Classification Search .................. 606/86, 606/92, 114, 115, 123, 170, 180, 213, 223, 606/93, 94; 604/35, 164.01, 523, 540, 541, 604/902, 313, 316, 93.01, 167.01, 167.02, 604/256, 104–106, 109, 117, 174, 178, 176, 604/179; 623/19.11; 600/577, 567, 565
See application file for complete search history.

(56) References Cited

U.S. PATENT DOCUMENTS 2,687,131 A * 8/1954 Raiche ................... 604/101.05
4,646,722 A * 3/1987 Silverstein et al. ......... 600/104

4,915,694 A * 4/1990 Yamamoto et al. ......... 604/180
4,969,870 A * 11/1990 Kramer et al. ........... 604/93.01

(Continued)

FOREIGN PATENT DOCUMENTS

DE 3108918 A1 9/1982

(Continued)

OTHER PUBLICATIONS

Pitto et al., Comparison of Fixation of the Femoral Component without Cement and Fixation with Use of a Bone-Vacuum Cementing Technique for the Prevention of Fat Embolism during Total Hip Arthoroplasty.

(Continued)

*Primary Examiner*—Brian E. Pellegrino
(74) *Attorney, Agent, or Firm*—Thomte Mazour & Niebergall; Shane M. Niebergall

(57) ABSTRACT

A tool for cementing a liner to the glenoid cavity of a scapula. The tool comprises an elongated, hollow, rigid tube having distal and proximal ends with the distal end of the tube having either an angular portion or a curved portion which has a plurality of openings formed therein. The tube has a length such that the distal end thereof may be positioned in the glenoid vault and so that the proximal end of the tube may be placed in communication with a source of suction. An elongated sleeve member is slidably mounted on the tube and preferably has a sealing gasket at its distal end which may be moved into sealing engagement with the coracoid process around the opening formed therein. A flexible obturator is selectively extended through the tube to clear the tube of debris.

9 Claims, 3 Drawing Sheets

U.S. PATENT DOCUMENTS

| | | | |
|---|---|---|---|
| 5,046,509 A * | 9/1991 | Kater | 600/577 |
| 5,196,003 A * | 3/1993 | Bilweis | 606/123 |
| 5,197,949 A * | 3/1993 | Angsupanich | 604/35 |
| 5,403,317 A | 4/1995 | Bonutti | |
| 5,417,654 A * | 5/1995 | Kelman | 604/22 |
| 5,489,310 A | 2/1996 | Mikhail | |
| 5,499,989 A * | 3/1996 | LaBash | 600/567 |
| 5,571,204 A | 11/1996 | Nies | |
| 5,693,030 A * | 12/1997 | Lee et al. | 604/170.03 |
| 5,704,909 A | 1/1998 | Morrey et al. | |
| 5,810,785 A * | 9/1998 | Bogert et al. | 604/167.02 |
| 6,019,753 A * | 2/2000 | Pagan | 604/523 |
| 6,048,346 A | 4/2000 | Reiley et al. | |

FOREIGN PATENT DOCUMENTS

| | | |
|---|---|---|
| DE | 4022985 A1 | 1/1992 |
| WO | WO 99/51149 | 10/1999 |
| WO | WO 9952441 A1 * | 10/1999 |
| WO | WO 01/10356 | 2/2001 |

OTHER PUBLICATIONS

PCT International Preliminary Examination Report dated Sep. 24, 2003 with International Search Report.

\* cited by examiner

METHOD AND MEANS FOR CEMENTING A LINER ONTO THE FACE OF THE GLENOID CAVITY OF A SCAPULA

CROSS-REFERENCE TO RELATED APPLICATION

This is a divisional application of Petitioner's earlier application Ser. No. 09/563,613 filed May 2, 2000, now U.S. Pat. No. 6,506,214 entitled "METHOD AND MEANS FOR CEMENTING A LINER ONTO THE FACE OF THE GLENOID CAVITY OF A SCAPULA".

BACKGROUND OF THE INVENTION

1. Field of the Invention

This invention relates to a method of cementing a liner onto the face of the glenoid cavity of a scapula and a tool which is used to perform the method.

2. Description of the Related Art

Humeral endoprostheses were introduced for the treatment of fractures of the proximal humerus and arthritis of the shoulder joint in the early 1950s. This operation evolved into a complete shoulder replacement with the addition of a high density polyethylene surface to cover the glenoid cavity which is located on the scapular side of the glenohumeral joint. Firm fixation of the polyethylene to the small glenoid cavity with acrylic cement called Methyl Methacrylate has been a constant problem. The complex mechanics of the shoulder joint accentuate this problem and frequently leads to loosening of the polyethylene liner. This difficulty has led many surgeons simply to return to the early surgery of a humeral endoprostheses and omit the polyethylene liner despite its superior pain relieving qualities.

SUMMARY OF THE INVENTION

The method of cementing a liner onto the face of the glenoid cavity of a scapula which includes a glenoid vault, and a coracoid process projecting from the scapula, comprises the steps of: (1) creating an opening in the coracoid process adjacent the outer end thereof which communicates with the medullary canal of the coracoid process; (2) creating an elongated bore in the medullary canal which extends from the opening in the coracoid process to the glenoid vault of the scapula; (3) inserting an elongated, hollow, rigid tube, having distal and proximal ends, through the opening and through the bore so that the distal end thereof is positioned in the glenoid vault; (4) placing the distal end of an elongated sleeve, which is slidably mounted on the tube, into sealing engagement with the outer end of the coracoid process; (5) applying suction to the proximal end of the tube to suction fluid and debris from the glenoid vault outwardly through the tube; (6) positioning cement on the face of the glenoid cavity and forcing cement into the glenoid vault while suction is applied to the tube; and (7) positioning the liner on the face of the glenoid cavity so that the liner is brought into contact with the cement.

The tool for performing the above-described method comprises an elongated, hollow, rigid tube having distal and proximal ends with the distal end of the tube having either an angular portion or a curved portion which has a plurality of openings formed therein. The tube has a length such that the distal end thereof may be positioned in the glenoid vault and so that the proximal end of the tube may be placed in communication with a source of suction. An elongated sleeve member is slidably mounted on the tube and preferably has a sealing gasket at its distal end which may be moved into sealing engagement with the coracoid process around the opening formed therein. A flexible obturator is selectively extended through the tube to clear the tube of debris.

It is therefore a principal object of the invention to provide an improved method of cementing a liner onto the face of the glenoid cavity of a scapula.

A further object of the invention is to provide a tool for use in cementing a liner onto the face of the glenoid cavity of a scapula.

These and other objects will be apparent to those skilled in the art.

DESCRIPTION OF THE PREFERRED METHOD AND EMBODIMENT

Figure 1:
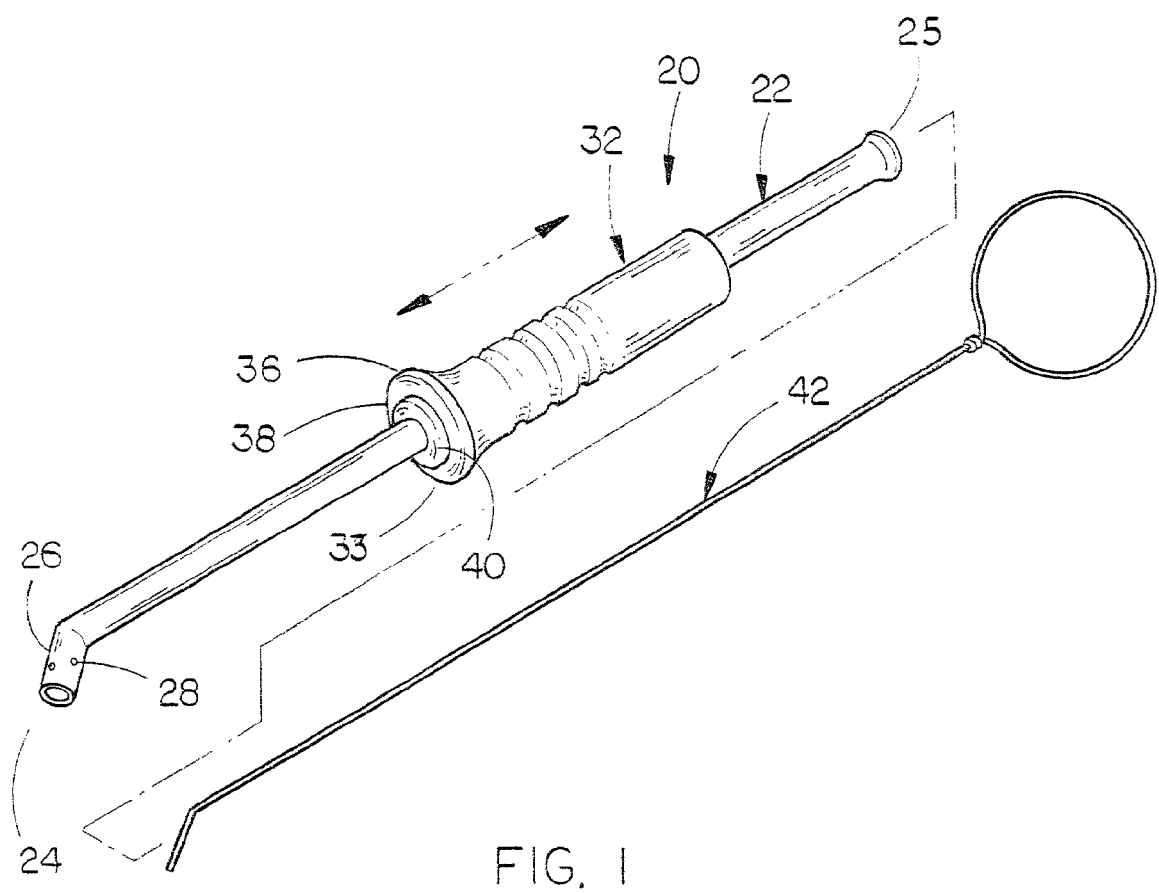
FIG. 1 is a perspective view of the apparatus of this invention.
Figure 2:
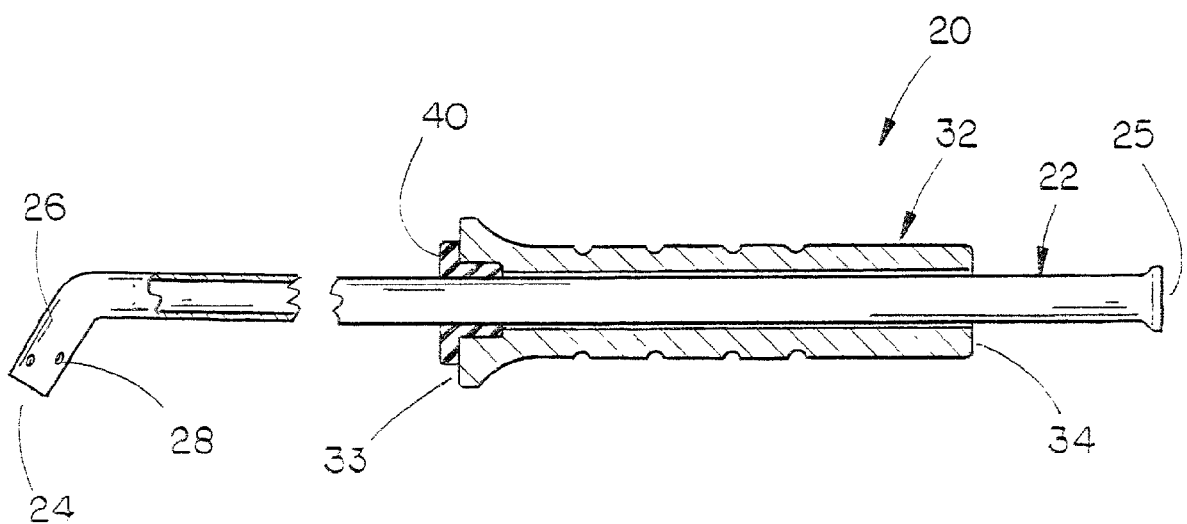
FIG. 2 is a partial longitudinal sectional view of the tool of FIG. 1.

In the drawings, the numeral 10 refers to the glenoid cavity of a scapula 12. The numeral 14 refers to the coracoid process which is a bony prominence on the anterior portion of the scapula which attaches just medial to the glenoid cavity. The coracoid process 14 includes a medullary canal 16 therein which is contiguous with the cancellous bone behind the glenoid cavity. The numeral 18 refers to the humerus of the glenohumeral joint. The numeral 19 refers to the glenoid vault in the scapula 12. The difficulty in cementing a high density polyethylene liner onto the face of the glenoid cavity 10 is the driving force behind the instant invention.

The tool which is used in the method described herein is referred to generally by the reference numeral 20 and comprises an elongated, hollow, rigid tube 22 having a distal end 24 and a proximal end 25. The distal end 24 of the tube 20 is provided with an angular portion 26 or an arcuate portion 26' that are preferably provided with a plurality of small openings 28 formed therein. The length of the tube 22 is such that the distal end 24 thereof may be positioned in the glenoid vault 19 and so that the proximal end 25 thereof may be placed in communication with a source of vacuum or suction, as will be described in more detail hereinafter.

The numeral 32 refers to an elongated sleeve which is slidably mounted on tube 22. Sleeve 32, for purposes of description, will be described as having a distal end 33 and a proximal end 34. As seen in the drawings, the distal end 33 is provided with a flared portion 36 which presents a sealing surface 38, as will be described hereinafter. Preferably, a sealing gasket 40 is provided at the end of flare 36 which is adapted to engage the coracoid process 14. An elongated flexible obturator 42 is provided which is adapted to be selectively extended through the tube 22 to keep tube 22 free of debris.

Figure 4:
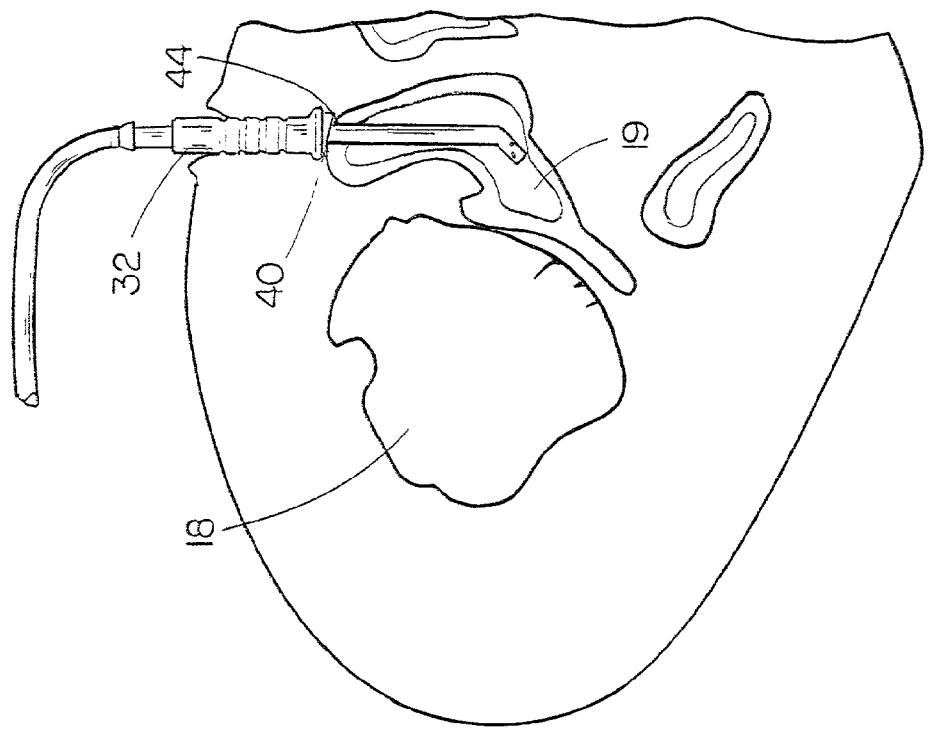
FIG. 4 is a view similar to FIG. 3 except that the tool is being inserted through the coracoid process at a somewhat different and FIG. 5 is a partial longitudinal sectional view of the tool of FIG. 2 with an alternately shaped distal end portion.
Figure 3:
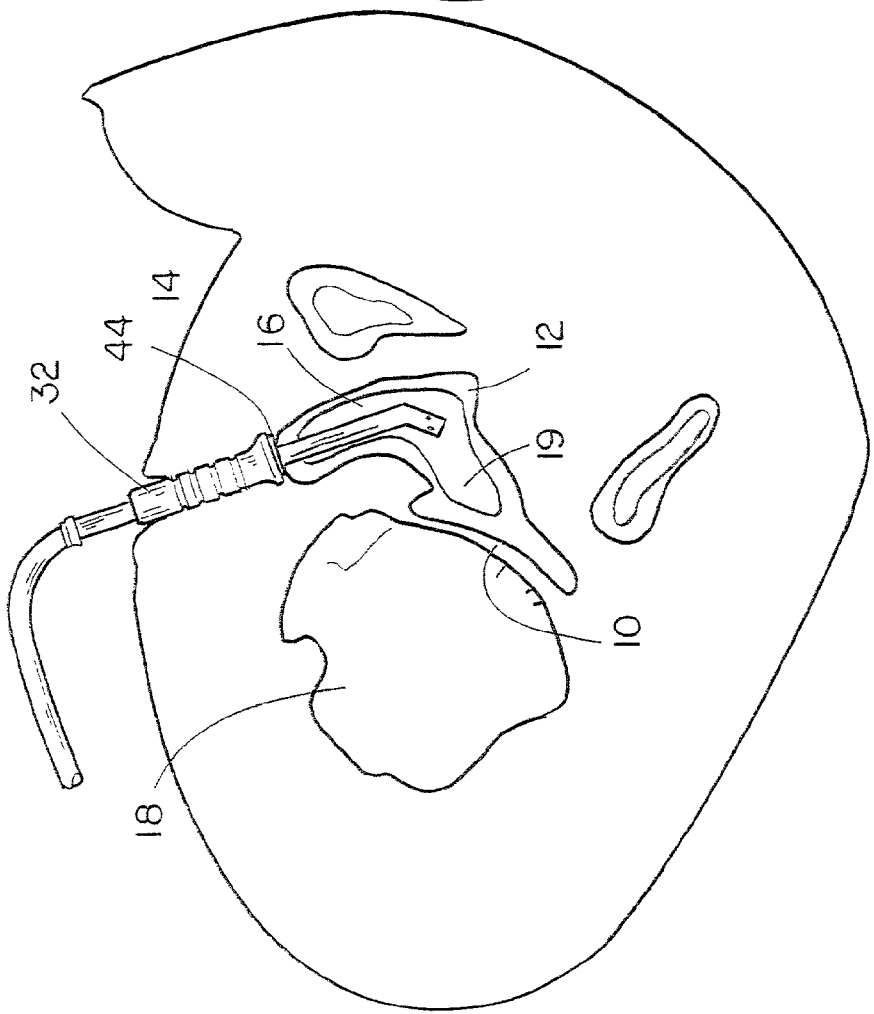
FIG. 3 is a view illustrating the tool of this invention being inserted through the medullary canal of a coracoid process.
Figure 5:
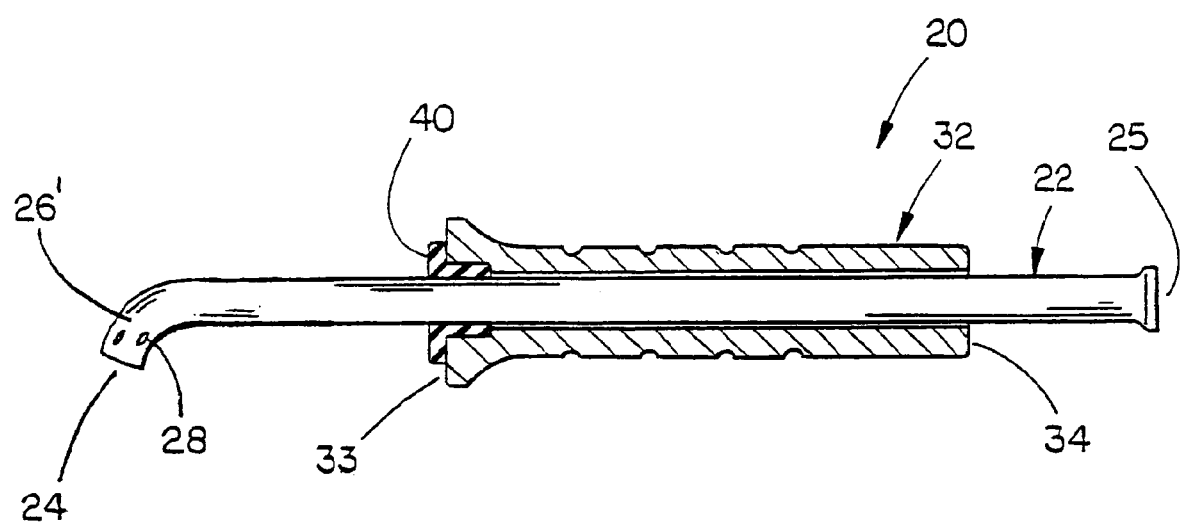

The method of utilizing the tool will now be described. First, an incision is created in the shoulder of the patient to expose the outer end of the coracoid process 14 and to provide access to the glenoid cavity 10. An opening 44 is then drilled through the outer end of the coracoid process 14 so that the opening communicates with the medullary canal 16. The medullary canal 16 is then hollowed out by the use of a curette or the like. Tube 22 is then inserted through the opening 44 and the hollowed out medullary canal 16 so that the distal end thereof is positioned in the glenoid vault 19, as illustrated in FIGS. 3 and 4. FIG. 4 illustrates the situation where the opening 44 is located somewhat laterally of the opening 44 in FIG. 3. The sleeve 32 is then preferably slidably moved on the tube 22 so that the gasket 40 sealably engages the outer end of the coracoid process 14 around the opening 44 created in the outer end of the coracoid process 14. The proximal end 25 of the tube 22 is then placed in communication with a source of suction or vacuum. The suction applied to the tube 22 sucks out the blood and fluids in the glenoid vault 19 to remove competing hydrostatic forces that arise when the surgeon pushes or compacts the cement into the glenoid vault 19 through the glenoid cavity 10. When the glenoid vault 19 has been cleared of blood, fluids, debris, etc., a drier surface in the glenoid vault 19 is provided and provides a more porous surface for the cement to adhere to. The surgeon then applies compressive force to the cement from the face of the glenoid cavity 10 to force the cement into the glenoid vault 19. The sucking or pulling force from the tube 22 adds to the compressive force insertion of the cement to literally pull the cement into the honeycombed cancellous bone of the glenoid vault 19. A high density polyethylene liner is then positioned on the face of the glenoid cavity 10 so as to be brought into contact with the cement thereon. Once the liner has sufficiently adhered to the cement, the tube 22 is removed. If required, the opening 44 at the outer end of the coracoid process 14 is then sealed.

Thus it can be seen that a novel method and means has been provided for enhancing the attachment of a high density polyethylene liner to the glenoid cavity.

Thus it can be seen that the invention accomplishes at least all of its stated objectives.

I claim:

1. A tool for insertion through the coracoid process and into the glenoid vault of a scapula, comprising:
    an elongated, rigid tube, having an exterior surface and an open interior portion that extends between distal and proximal ends; said tube having a length and diameter such that its distal end may be positioned in the glenoid vault and so that its proximal end may be placed into communication with a suction mechanism;
    an elongated sleeve operatively coupled with said tube in a manner that permits selective, sliding movement of said sleeve along a length of the exterior surface of said tube; said sleeve having proximal and distal ends and a sealing face on said distal end that is generally transverse to a long axis of said elongated sleeve; and
    a gasket operatively coupled to the distal end of said sleeve and the exterior surface of said tube in a manner that permits selective, sliding movement of said gasket along a length of the exterior surface of said tube; said gasket being positioned in a manner that establishes a seal between the distal end of said sleeve and the exterior surface of said tube; said gasket being further positioned across a substantial portion of the sealing face on the distal end of said sleeve and shaped and sized to permit selective sealing engagement with the coracoid process when the distal end of said tube is positioned in the glenoid vault.

2. The tool of claim 1 wherein said distal end of said tube has a plurality of openings formed therein.

3. The tool of claim 1 wherein said distal end of said tube has an arcuate portion.

4. The tool of claim 1 wherein said tube is provided with an angular bend, adjacent the distal end of said tube, so that the open interior portion of said tube extends along a non-linear path between said proximal and distal ends.

5. The tool of claim 1 further including a flexible obturator which may be selectively extended through said tube to clear said tube of debris.

6. The tool of claim 1 further comprising a suction mechanism, capable of generating a suction force, operatively coupled with the proximal end portion of said tube.

7. The tool of claim 4 wherein the proximal end of said tube is shaped and sized to have a diameter greater than an intermediate portion of said tube; said bend, adjacent the distal end of said tube, and the proximal end of said tube being shaped and sized relative to said tube to substantially prevent unintended removal of said sleeve from said tube.

8. The tool of claim 7 wherein said distal end of said tube has a plurality of openings formed therein.

9. The tool of claim 8 further including a flexible obturator which may be selectively extended through said tube to clear said tube of debris.

* * * * *